United States Patent [19]
Galli Angeli

[11] Patent Number: 5,932,589
[45] Date of Patent: Aug. 3, 1999

[54] ANTITUSSIVE COMPOSITION CONTAINING DEXTROMETHORPHAN AND BENZYDAMINE

[75] Inventor: Depalmo Galli Angeli, Falconara Marittima, Italy

[73] Assignee: Aziende Chimiche Riunite Angelini Francesco A.C.R.A.F. S.p.A., Rome, Italy

[21] Appl. No.: 08/700,362

[22] PCT Filed: Feb. 22, 1995

[86] PCT No.: PCT/EP95/00658

§ 371 Date: Dec. 24, 1996

§ 102(e) Date: Dec. 24, 1996

[87] PCT Pub. No.: WO95/23602

PCT Pub. Date: Sep. 8, 1995

[30] Foreign Application Priority Data

Mar. 1, 1994 [IT] Italy ................................. MI94A0362

[51] Int. Cl.⁶ ......................... A61K 31/44; A61K 31/415
[52] U.S. Cl. ........................... 514/289; 514/403; 514/850
[58] Field of Search ..................................... 514/289, 403, 514/850

[56] References Cited

U.S. PATENT DOCUMENTS 5,196,436  3/1993  Smith ....................................... 514/289

OTHER PUBLICATIONS

Budavari, S. et al., "The Merck Index" (11$^{th}$ Ed.) Merck & Co., Inc., Rahway, N.J. (1989), pp. 175–176.
Hartung–Brooks, On Continuing Practice, vol. 17, No. 1 (Jan. 1990) pp. 2–6.

*Primary Examiner*—M. Moezie
*Attorney, Agent, or Firm*—Oblon, Spivak, McClelland, Maier & Neustadt, P.C.

[57] ABSTRACT

Oral antitussive pharmaceutical composition which allows a significant contact of its components with mucous membranes of the buccal cavity and comprises a centrally acting antitussive or a pharmaceutically acceptable salt thereof and benzydamine or a pharmaceutically acceptable acid addition salt thereof.

4 Claims, No Drawings

ANTITUSSIVE COMPOSITION CONTAINING DEXTROMETHORPHAN AND BENZYDAMINE

This application is a 371 of PCT/EP95/00658 filed Feb. 22, 1995.

DESCRIPTION

This invention relates to an antitussive composition.

More particularly, this invention relates to an oral antitussive composition, characterized in that it comprises a centrally acting antitussive or a pharmaceutically acceptable salt thereof and benzydamine or a pharmaceutically acceptable acid addition salt thereof.

Coughing is a physiological action heplful to free the respiratory tract from foreign substances and from excess secretions. In some cases however, coughing performs no useful purpose, and instead anger the patient or prevent his or her rest or sleep. This leads to the need for administering a drug capable of reducing the recurrence and/or severity of coughing.

Among the many drugs which reduce coughing some act on the central nervous system. Examples of such antitussives are: codeine, dextromethorphan, dihydrocodeine, dimemorfan, noscapine, levopropoxyphene napsylate, carbetapentane, caramiphen, chlophedianol, diphenhydramine, glaucine, benzonatate, hydrocodone and hydromorphone. The most commonly used of these are: codeine, dextromethorphan, dihydrocodeine, dimemorphan and noscapine.

Dextromethorphan is a particularly significant example of a non-narcotic, centrally acting antitussive (The Merck Index, 9th ed., 1976, page 1289, No. 8116). The average dose of dextromethorphan hydrobromide to be given to adults is of 15 to 30 mg, 3–4 times a day (Goodman & Gilman—"le basi farmacologiche della terapia"—8th italian edition, Zanichelli—Bologna). It is available in dragees, tablets, syrups and drops, alone or in association with balsamic-expectorant products.

Benzydamine (The Merck Index, 9th Edition, 1976, page 147, No. 1136) was disclosed for the first time by U.S. Pat. No. 3,318,905 which relates to a group of products having analgesic, anti-inflammatory and muscle relaxant activity. It has been widely utilized in human therapy as hydrochloride. As far as the systemic route is concerned, it is mainly utilized as anti-inflammatory and analgesic agent, by topical route it is however mainly utilized in those pathologies which involve local inflammation such as, for example, myalgia, tendonitis, vulvovaginitis, gingivitis, stomatitis, inflammation of mucosa of the buccal cavity and the like.

It has now unexpectedly been found that benzydamine and pharmaceutically acceptable acid addition salt thereof are capable of shortening the onset time of the action of centrally acting antitussives on the peripheral stimulus of the cough in particular pathologies compared to the antitussive alone.

This unexpected effect has been proved by clinical trials in human.

Therefore, it is a first object of this invention to provide an oral antitussive pharmaceutical composition, characterized in that:

it allows a significant contact of its components with the mucous membranes of the buccal cavity, and comprises a centrally acting antitussive or a pharmaceutically acceptable salt thereof and benzydamine or a pharmaceutically acceptable acid addition salt thereof.

For example, dextromethorphan alone performs its action in 20–30 minutes (H. Matthys, B. Bleicher et al.; J. Int. Med. Res., 11, 92–100, 1983).

However, when it is administered in association with benzydamine or a pharmaceutically acceptable acid addition salt thereof, in a pharmaceutical dosage form which allows a significant contact of its components with the mucous membranes of the buccal cavity, it reduces the cough symptom in a much shorter time, that is to say in a few minutes.

Examples of suitable pharmaceutical dosage forms which allow a significant contact of their components with the mucous membranes of the buccal cavity are pastilles, sweets, chewable tablets and chewing gums.

In addition to benzydamine or an acid addition salt thereof, such as hydrochloride, and a centrally acting antitussive or a pharmaceutically acceptable salt thereof, the compositions of this invention comprise a solid or fluid inert diluent or vehicle and, optionally, other additives suitable for pharmaceutical use, and are prepared by conventional techniques.

Examples of suitable additives are sweeteners, flavourings and dyes.

In the composition of this invention, the effective dose of benzydamine and of a centrally acting antitussive will range depending on various factors that are well known to the persons skilled in the art such as the antitussive used, individual response, age and general health condition of the patient.

In general, however, the composition of this invention will comprise an amount of a centrally acting antitussive of from 0.5 to twice the standard dose thereof or the equivalent amount of a pharmaceutically acceptable salt thereof.

In this description the term "standard dose" is intended to mean the effective dose which is usually administered by oral route for each individual centrally acting antitussive.

For example, in the case of dextromethorphan, the effective dosage ranges from 5 to 30 mg per each administration depending on whether the treatment (1–6 times a day) is for children or adults. In some cases, however, single doses of 60 mg were also administered (Goodman & Gilman, 7th italian ed., page 486).

As far as benzydamine is concerned, the amount which proved to be capable of reducing the onset time of the action of the centrally acting antitussive on the peripheral stimulus of the cough ranges depending on the specific antitussive and pharmaceutical dosage form that are used.

Typically, as regards benzydamine, the pharmaceutical compositions of this invention will comprise (a) an amount by weight of from 1/200 to twice the amount by weight of the centrally acting antitussive, or (b) the equivalent amount of a pharmaceutically acceptable acid addition salt thereof.

A first preferred composition of this invention comprises from 0.15 to 10 mg of benzydamine and from 5 to 30 mg of dextromethorphan or equivalent amounts of pharmaceutically acceptable salt thereof.

Finally, the pharmaceutical compositions of this invention can also comprise further active ingredients whose utility in association with centrally acting antitussives is known.

Typical examples of said active ingredients are antihistamines and balsamic agents.

The following examples are intended to illustrate this invention without, however, limiting it.

EXAMPLE 1

Chewable Tablets

Each 1.37 g tablet contains:

| | |
|---|---|
| Benzydamine hydrochloride | 3.0 mg |
| Dextromethorphan hydrobromide, hydrate | 7.5 mg |
| Mannitol | 1121.5 mg |
| Maltol | 200.0 mg |
| Magnesium trisilicate | 67.5 mg |
| Magnesium stearate | 15.5 mg |
| Ammonium glycyrrhizinate | 15.0 mg |
| Aspartame | 15.0 mg |
| Balsamic flavour | 15.0 mg |
| Glycerol palmitic-stearic ester | 10.0 mg |

This tablet is prepared by the method of direct compression; the active ingredients are premixed in order to ensure uniformity of the content in finished product.

Maltol and part of mannitol are placed in a Zanchetta™ mixer.

Benzydamine hydrochloride and dextromethorphan hydrobromide monohydrate, adsorbed by 10% on magnesium trisilicate, are placed in a smaller mixer and then balsamic flavour, aspartame, ammonium glycyrrhizinate and the remaining mannitol are added.

The mixture is blended for approximately 15 minutes and then transferred into the mixer containing mannitol and maltol.

Afterwards magnesium stearate and glycerol palmitic-stearic ester are added and mixed to homogeneity for 30 minutes, approximately.

The mixture is compressed by a rotating machine equipped with punches (20.5×11.5 mm).

EXAMPLE 2

Sweets

Each 5 g sweet contains:

| | |
|---|---|
| Benzydamine hydrochloride | 3.0 mg |
| Dextromethorphan hydrobromide | 7.5 mg |
| Lycasin 80/55 | 4165.0 mg |
| Arabic gum | 79.0 mg |
| Mannitol | 725.0 mg |
| Natural flavours | 20.3 mg |
| Natural dye | 0.2 mg |

Example 3

| | |
|---|---|
| Benzydamine hydrobromide | 3.0 mg |
| Dextromethorphan hydrobromide | 7.5 mg |
| Saccharose | 3052.5 mg |
| Glucose | 1920.0 mg |
| Mint | 12.0 mg |
| Menthol | 4.8 mg |
| Natural dyes | 0.2 mg |

I claim:

1. An oral antitussive pharmaceutical composition, which comprises from about 3.0 mg of benzydamine or an equivalent amount of the hydrochloride or hydrobromide salt thereof, and about 7.5 mg of dextromethorphan or an equivalent amount of the hydrobromide or hydrobromide hydrate salt thereof.

2. The composition of claim 1, which comprises 3.0 mg of benzydamine hydrochloride and 7.5 mg dextromethorphan hydrobromide hydrate.

3. The composition of claim 1, which comprises 3.0 mg of benzydamine hydrochloride and 7.5 mg of dextromethorphan hydrobromide.

4. The composition of claim 1, which comprises 3.0 mg of benzydamine hydrobromide and 7.5 mg of dextromethorphan hydrobromide.

* * * * *